US006330354B1

(12) United States Patent
Companion et al.

(10) Patent No.: US 6,330,354 B1
(45) Date of Patent: *Dec. 11, 2001

(54) METHOD OF ANALYZING VISUAL INSPECTION IMAGE DATA TO FIND DEFECTS ON A DEVICE

(75) Inventors: Pierre M. Companion, Winooski; Karl K. Moody, III, Essex Junction; Brenda M. Wilson, Hinesburg, all of VT (US)

(73) Assignee: International Business Machines Corporation, Armonk, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/847,011

(22) Filed: May 1, 1997

(51) Int. Cl.[7] ............................................. G06K 9/00
(52) U.S. Cl. .................... 382/150; 382/151; 382/147; 382/149; 382/174
(58) Field of Search .................... 382/150, 151, 382/145, 147, 148, 149, 162, 174

(56) References Cited

U.S. PATENT DOCUMENTS

| 3,916,439 | | 10/1975 | Lloyd et al. ........................ 348/130 |
| 4,319,845 | * | 3/1982 | Shuji ................................... 356/399 |
| 4,441,124 | * | 4/1984 | Heebner et al. .................... 358/106 |
| 4,587,617 | | 5/1986 | Barker et al. ....................... 382/149 |
| 4,589,140 | | 5/1986 | Bishop et al. ....................... 382/148 |
| 4,633,504 | * | 12/1986 | Wihl .................................... 356/390 |
| 4,648,053 | * | 3/1987 | Fridge ................................. 382/147 |
| 4,688,939 | * | 8/1987 | Ray .................................... 250/572 |
| 4,740,708 | * | 4/1988 | Batchelder ......................... 250/572 |
| 4,809,341 | | 2/1989 | Matsui et al. ...................... 382/149 |
| 4,845,764 | * | 7/1989 | Ueda et al. ............................ 382/8 |
| 4,851,902 | * | 7/1989 | Tezuka et al. ...................... 358/101 |
| 4,860,371 | | 8/1989 | Matsuyama et al. ............... 382/149 |
| 5,003,615 | | 3/1991 | Seitz ................................... 382/108 |
| 5,012,502 | * | 4/1991 | Battin et al. .......................... 378/58 |
| 5,023,917 | | 6/1991 | Bose et al. ......................... 382/149 |
| 5,054,097 | * | 10/1991 | Flinois et al. ........................ 382/47 |
| 5,058,178 | * | 10/1991 | Ray .................................... 358/106 |
| 5,093,797 | * | 3/1992 | Yotsuya et al. .................... 364/552 |
| 5,103,304 | | 4/1992 | Turcheck, Jr. et al. ............ 348/130 |
| 5,146,509 | | 9/1992 | Hara et al. .......................... 382/149 |
| 5,163,128 | | 11/1992 | Straayer ............................. 345/589 |
| 5,172,420 | | 12/1992 | Ray et al. ........................... 382/150 |
| 5,311,598 | * | 5/1994 | Bose et al. .............................. 382/1 |

(List continued on next page.)

OTHER PUBLICATIONS

IBM/ vol. 27/No. 10A/ Mar. 1985/Dynamic Chip Pad Volume Analysis Tool.

William M. Silver, Congnex Corp. "Golden Template Comparison" The Journal of Machine Perception, vol. 7, No. 11, p. 20–24 Oct. 1990.*

William M. Silver "Golden Template Comparison", Sensors the journal of machine perception, Oct. 1990, vol. 7 No. 11, Oct. 15, 1999.*

Primary Examiner—Matthew C. Bella
Assistant Examiner—Sheela Chawan
(74) Attorney, Agent, or Firm—James M. Leas

(57) ABSTRACT

A method for analyzing image data is disclosed that will find defects on a multi-layer device having solder pads, such as a semiconductor computer chip. The method provides a device template image, a theoretical image created from data from several real images, for comparison to an image of a device to be tested after the solder pad data is segmented. The parameter values of the device to be tested are recorded and compared to the parameter values of the device template, forming a difference image. The difference image and the solder pad data are then run through a series of tests, wherein the device is determined defective or not defective.

17 Claims, 8 Drawing Sheets

U.S. PATENT DOCUMENTS

| | | | | |
|---|---|---|---|---|
| 5,351,201 | * | 9/1994 | Harshbarger, Jr. et al. | 348/187 |
| 5,440,396 | | 8/1995 | Markus et al. | 356/394 |
| 5,455,870 | * | 10/1995 | Sepai et al. | 382/131 |
| 5,475,766 | | 12/1995 | Tsuchiya et al. | 382/144 |
| 5,548,326 | * | 8/1996 | Michael | 382/86 |
| 5,640,199 | * | 6/1997 | Garakani et al. | 382/87 |
| 5,640,200 | * | 6/1997 | Michael | 348/86 |
| 5,692,070 | * | 11/1997 | Kobayashi | 382/141 |
| 5,719,951 | * | 2/1998 | Shackleton et al. | 382/118 |
| 5,760,829 | * | 6/1998 | Sussmeier | 348/180 |
| 5,850,466 | * | 12/1998 | Schott | 382/148 |

* cited by examiner

ECCENTRICITY

RELATIVE AREA

ALIGNMENT

BOUNDS

CONVEXITY

METHOD OF ANALYZING VISUAL INSPECTION IMAGE DATA TO FIND DEFECTS ON A DEVICE

BACKGROUND OF THE INVENTION

1. Technical Field

The invention relates generally to testing of circuit devices, and more specifically, to analyzing image data to find defects on a device.

2. Background Art

Advances in integrated circuits have enhanced the ability to integrate increasingly more circuits on a single chip. As the circuit complexity on a chip increases, so does the need to thoroughly test the chip for defects caused through manufacture processing, misalignment of circuit elements, improper dicing, environmental factors, such as dirt, heat, etc. At the present, the common method of testing semiconductor chips is to visually inspect the chip for defects, which are found through color and size gradients. Many of the defects to date can only be found by manual examination, allowing for fatigue and human error. That is, examinations have been done manually because of the intricacies and complexities involved in thoroughly testing the various layers of a semiconductor computer chip, and in the cases of expensive and important equipment the percent of error should be minimal.

Automated systems have been developed for the testing of larger devices with a few layers, such as the ceramic chip. Because the circuitry has only a few, accessible layers, the devices are easily tested against a reference pattern, and categorized as falling within the required standards or not. Examples of automated systems testing with a reference pattern include: U.S. Pat. No. 5,172,420 "Method for Monitoring the Dimensions and Other Aspects Linewidth Thickness and Discoloration of Specular Patterns" (issued Dec. 15, 1992 to Ray et al. and assigned to AT&T Bell Laboratories); U.S. Pat. No. 5,146,509 "Method of Inspecting Defects in Circuit Pattern and System for Carrying Out the Method" (issued Sep. 8, 1992 to Hara et al. and assigned to Hitachi, Ltd.); U.S. Pat. No. 5,103,304 "High-Resolution Vision System for Part Inspection" (issued Apr. 7, 1992 to Turcheck, Jr. et al. and assigned to FMC Corp.); U.S. Pat. No. 5,023,917 "Method and Apparatus for Pattern Inspection" (issued Jun. 11, 1991 to Bose et al. and assigned to AT&T Bell Lab.); U.S. Pat. No. 4,648,053 "High Speed Optical Inspection System" (issued Mar. 3, 1987 to Fridge and assigned to Kollmorgen Technologies, Corp.); U.S. Pat. No. 4,587,617 "Image Inspection System for Defect Detection" (issued May 6, 1986 to Barker et al. and assigned to Cambridge Instruments Ltd.); and U.S. Pat. No. 5,475,766 "Pattern Inspection Apparatus With Ocrner Rounding of Reference Pattern Data" (issued Dec. 12, 1995 to Tsuchiya et al. and assigned to Kabushiki Kaisha Toshiba).

Although the aforementioned patents automatically test circuit boards with a reference pattern, having one set reference pattern for testing smaller devices, such as semiconductor chips, would result in many false positives (i.e., results that indicate a chip is defected, when in fact the chip still falls within an acceptable range of operability). False positives would most likely occur because the above-mentioned patents can only handle a couple of layers, repetitive pattern sequences, or specific shape/size measurements of the chip components. Furthermore, since there are numerous amounts of defects that could occur on any level of a multi-layer device, pattern testing that is created for a few exposed layers is not sophisticated enough to recognize the subtle defects, or even the larger defects on the lower levels of the multi-layered device that may be disastrous to the operability of the device. Finally, none of the patents address testing devices with solder pads, which are vital in communicating with the outside world.

Accordingly, a need has developed in the art for a method to automatically test an image for defects in a small, multi-layered device having a solder pad, such as a semiconductor computer chip.

SUMMARY OF THE INVENTION

It is thus an advantage of the present invention to provide a method to test small, multi-layered devices with a minimal amount of false positive results.

It is yet another advantage of the present invention to provide a method to successfully test devices having solder pads.

The foregoing and other advantages of the invention are realized by a method that provides a device template image (s), a theoretical image created from data from an averaged set of real images that are obtained from known good devices, for comparison to an image of a device to be tested after the solder pad data is segmented. Parameter values of the device to be tested are recorded and compared to the parameter values of the device template, forming a difference image. The difference image and the solder pad data are then run through a series of tests, wherein the device is determined defective or not defective.

The foregoing and other features and advantages of the invention will be apparent from the following more particular description of preferred embodiments of the invention, as illustrated in the accompanying drawings.

BRIEF DESCRIPTION OF THE DRAWINGS

The preferred exemplary embodiments of the present invention will hereinafter be described in conjunction with the appended drawings, where like designations denote like elements, and.

DETAILED DESCRIPTION OF THE DRAWINGS

Figure 1:
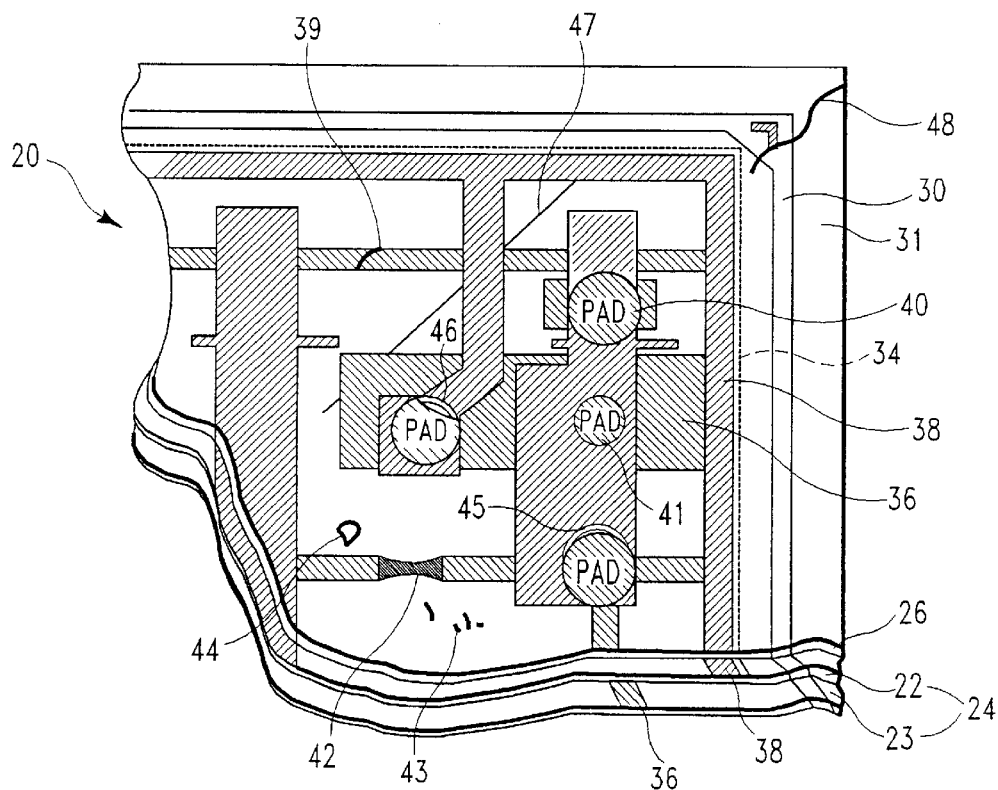
FIG. 1 is a block diagram of a portion of a semiconductor computer chip, illustrating the aspects and some defects to be tested by the method of the present invention.

A section of a semiconductor computer chip 20 is illustrated in FIG. 1. The device 20 comprises multiple alternating layers 24 of metal 23 and passivation layers 22, such as silicon dioxide. For illustration purposes, a single metal (M1) 36, along with the last layer of metal (LM) 38, is shown, but it is to be understood that several layers and arrays of metal (M1/M2) may be used in a semiconductor computer chip. The LM 38 is covered by a final coating of passivation 26, such as a nitride layer and/or polyimide layer. A nitride trench 30 surrounds the active layers of the device, separating the active layers from the inactive layers, or kerf region 31. A ground strap 34 provides common ground to the circuitry of the device. Solder pads 40 connect the metal 38 to the outside world.

As aforementioned, many defects may occur on a device through manufacture processing, dicing, environment, etc. In some instances, the imperfections on the device, such as small pieces of foreign material (FM) 43 will not affect the device performance. Overall, though, most defects on a device will impede the performance of the device. Some of the more common defects include Edge Chipping & Cracking (ECC) that produces defects such as hairline crack 48, Passivation Mechanical Damage (PMD) 44, corroded metal 42, exposed solder vias 46, misaligned solder pads 45, and a low volume solder pads 41. Other defects that are more subtle include thin cracks in LM 39 and Chemical Mechanical Polish (CMP) scratches 47. The failure to detect such defects may be severely damaging to the system containing the semiconductor device and its surrounding environment. Thus, creating an automated analysis system greatly reduces the error caused by the fatigue of manual analysis and skill level of the analyst.

Figure 2A:
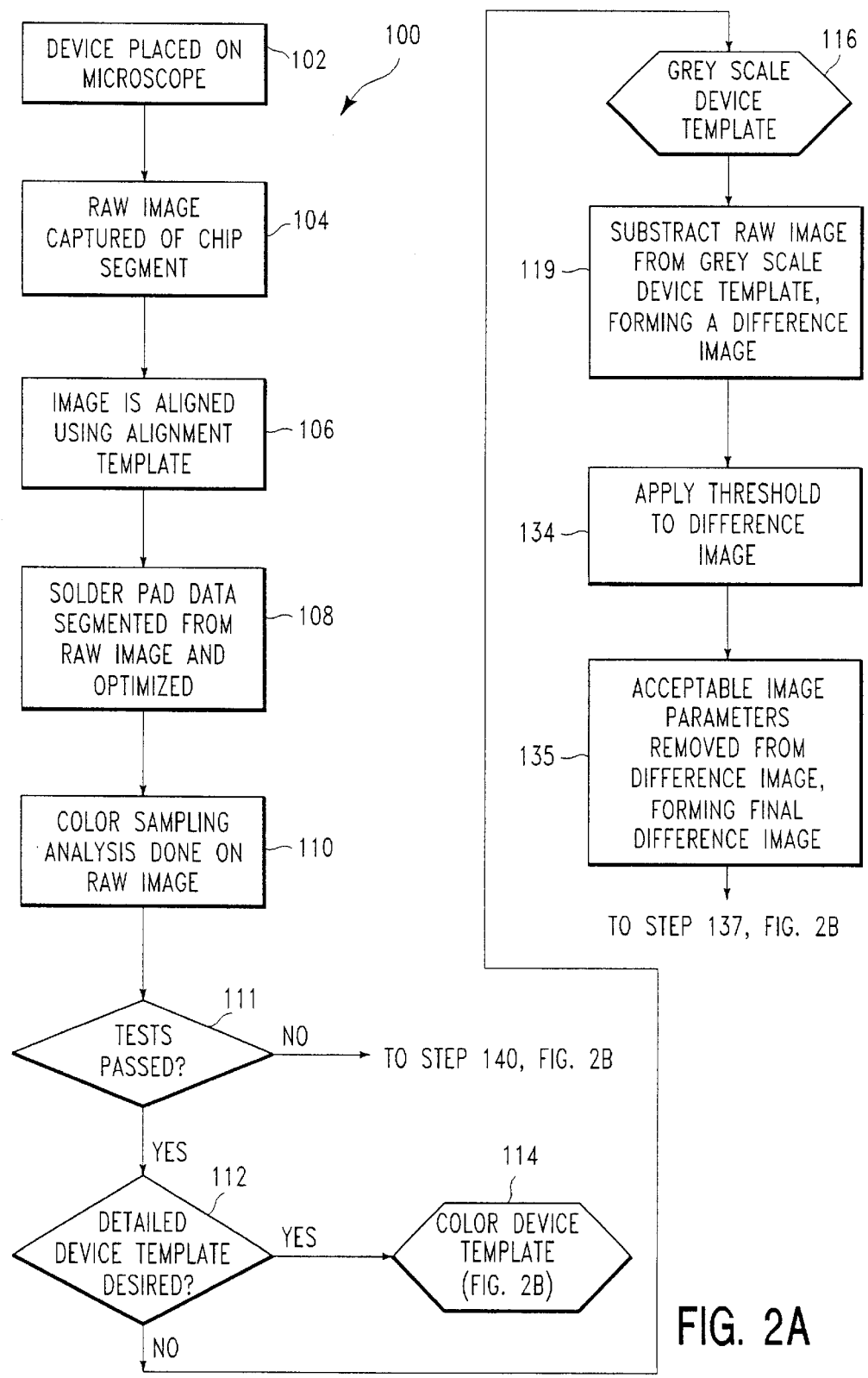
FIGS. 2A and 2B are flow diagrams illustrating a process of capturing and analyzing an image of a device in accordance with a preferred embodiment of the present invention.
Figure 2B:
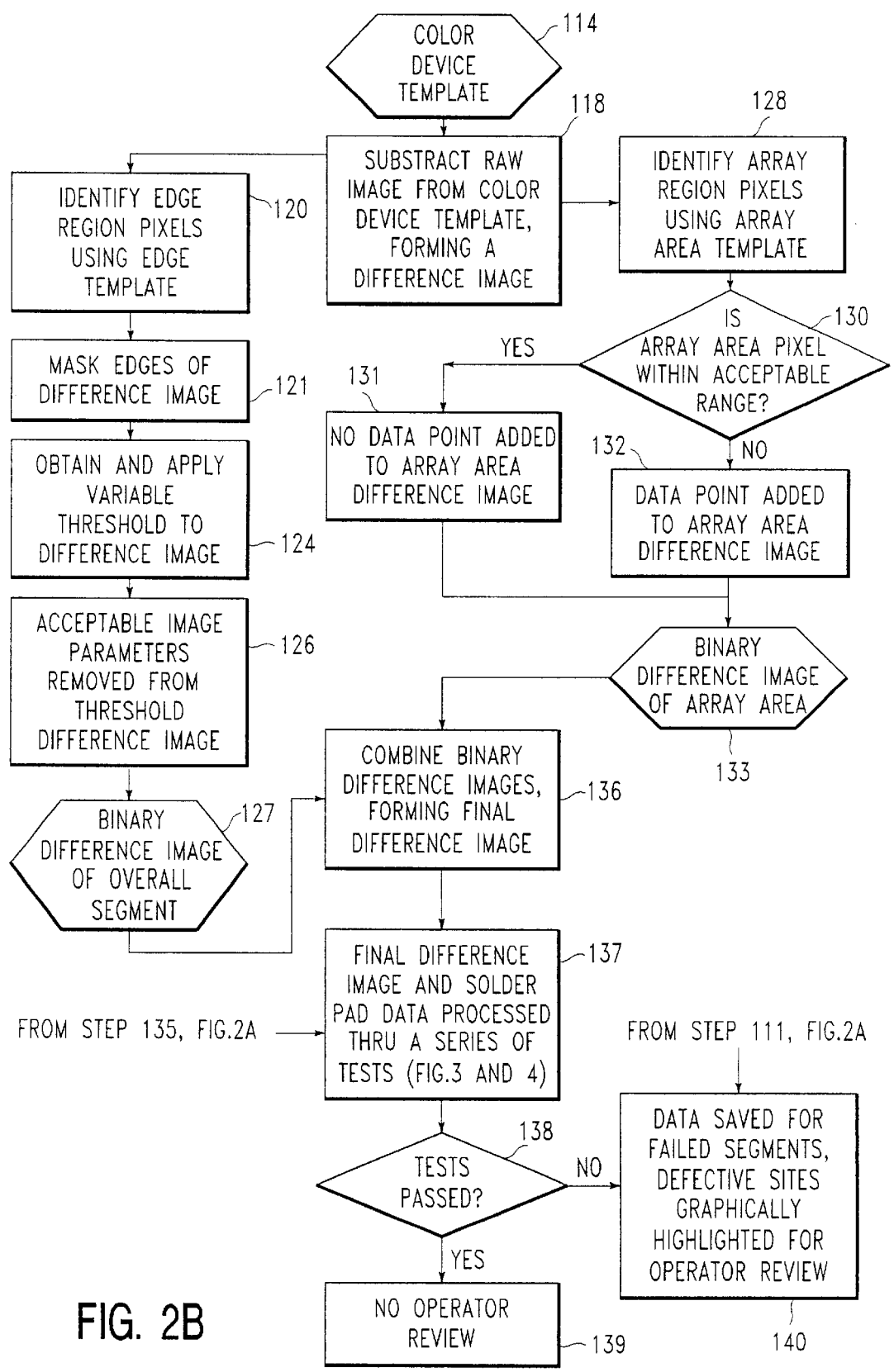

FIGS. 2A and 2B illustrate the process of automatic analysis of a device 20 such as a semiconductor chip. As seen in FIG. 2A, first the device is placed on a stage in a microscope (step 102). The device is mechanically aligned either by an alignment of the corner of the device, or, if the corner is off, by an alignment of the nitride trench 30 (FIG. 1). An image of the device is then created by using an image capturing software utility. The Z axis of the stage is adjusted to position and focus the device, and this focusing can be accomplished either automatically or manually. When the device is in optimum focus, a raw image is captured and stored in memory segment by segment until data for all regions of interest on the chip is collected (step 104). A segment is a rectangular portion of a field of view of the device in the microscope. Other means to obtain image data, such as line scanning, may also be used.

Associated with each segment is a text file, called a segment profile, that includes segment boundaries (the portion of the field of view that defines the segment); structure locations (the location of structures requiring additional inspection, such as C4 pads, ground straps, or nitride trenches); alignment coordinate data (the coordinates of a structure used for alignment within each segment); and segment periphery type (corner, edge or interior).

In the case where a group of devices on a single tray are being tested, some of the devices may be misaligned even though the majority of devices may line up with a mechanical alignment of the tray or device. Thus, along with the mechanical alignment, the raw images of the devices are software aligned (step 106) using an alignment template, a theoretical template of the ideal alignment position(s). Specifically, an alignment device aligns an actual LM image to the alignment template's LM image. First, an X/Y alignment is attempted, and, in the few cases where an X/Y alignment fails, a theta (θ) alignment is attempted. If the alignment device cannot align the LMs within a certain confidence level, the image fails the alignment test, indicating a miscut of the device. Devices that are miscut have kerf size differences that require X/Y data shifts that exceed specific correction limits. The correction limits are set within alignment profiles which are built for each segment of the alignment template to accommodate minor chip presentation differences.

The solder pad data is then segmented from the raw image (step 108), that is, the data from the solder pads are first retained in a separate image and the other image elements are removed, and then the solder pad data is extracted from the raw image.

Next, a first image parameter value having a first image criterion is collected from the raw image to detect gross defects (step 110). In this example, the first image parameter value is color, and the first image criterion is the range of acceptable colors. The colors of key areas on the device, including wide LM lines, the nitride trench, arrayed and blank regions, are imaged, stored, and analyzed for major defects. LM color values should be within a certain range as defined in the first image criterion. For example, LM lines should appear yellow/green beneath the poly/nitride. If the device missed a production step, such as the removal of a process film, (i.e., a Ti/Ni Cap) LM lines would appear as dark orange/brown lines. Analysis of the color of wide LM lines allows defects such as these to be detected. Thus, in color analysis, a predetermined quantity of raw image pixels specified in the segment profile are analyzed in each segment of the device and compared to an expected range of values found. If the values fall outside of the expected range (step 111=no), there is a good probability that the device was from a wafer that was grossly misprocessed during its build in the device fabricator, and the test will fail.

If the values of the color analysis fall within the expected range (step 111=yes), a device template is selected based on the detail desired for device analysis (step 112). In general, the device template is a theoretical image having device template parameter values for corresponding pixels, which are created from mathematical averages of at least 5 real images of good devices. Typically at least 10 images of good devices are included in the average. Each real image is first analyzed to insure there are no defects and then thresholded by applying a variable threshold value. For example, each pixel on each good device may be imaged as a color value, and this color value is converted to a grey scale value. The grey scale value is then converted to either black or white depending on whether the grey scale value of the pixel is above or below a preselected grey scale value, that preselected gray scale value being the threshold value. The thresholded images are then mathematically averaged to create the device template image for that segment. The devices used to obtain the device template image contain no solder pads, thus allowing for more accuracy of defect detection near the base of the solder pad and throughout the device. The data for each pixel on the device template may also be a range of acceptable values of each pixel of the device template parameter values, the range derived from the measure variation of the good devices.

The device template image may be as complex or simplistic as needed, preserving only those features and parameters desired to be tested. For example, if a fast, cursory testing of the defects is desired (step 112=no), a grey scale device template is created (step 116) that preserves only the high contrast parameters of each segment such as LM lines, polyimide edges, shape, size, and color. If a thorough testing of the device is desired (step 112=yes), a color device template is created (step 114) that preserves the subtle parameters of the array area. Preservation of the array area data detects subtle internal reliability defects such as small regions of residual resist, missing M1/M2 lines, corrosion of M1/M2 lines, and other defects typically caused by wafer wet/hot fabricator processes.

When using the grey scale device template (step 116), the parameter values of the raw image are subtracted from the grey scale device template parameter values for corresponding pixels to provide difference image elements for each of the corresponding pixels, the plurality of difference image elements creating a difference image (step 119). A threshold value is then applied to the difference image (step 134). The threshold value may be a variable threshold value, as discussed in greater detail with reference to the color device template, or a predetermined, constant threshold value. A second range of acceptable values for the device template parameter values for the plurality of pixels is provided, and the difference image elements of the difference image within the second range are then deleted (step 135) by removing trace lines resulting from normal process variations and imperfect alignment, thus, forming a final corrected difference image. These trace lines are horizontal, vertical, or 45 degree lines. They are also narrow compared to the width of the line on the device under test because they are the result of the difference between the line on the device under test and the line on the template. They are identified through the application of a Hough transform.

As shown in FIG. 2B, when using the color device template (step 114), the parameter values of the raw image are subtracted from the color device template parameter values using the Euclidian distance of the color components for corresponding pixels to provide difference image elements for each of the corresponding pixels, the plurality of difference image elements creating a difference image (step 118). The difference image elements of the difference image are then compared to an array area template (step 128) and an edge template (step 120). The array area template is formed by using color segmentation to extract the array area elements in the color device template. Color segmentation is the isolation of regions of an image from other regions based on color value. The array area template is used as a reference to identify the array regions in the original raw image of the inspected device (step 128). Each one of the array region pixels is then compared to a predetermined range of values (step 130). If the array region pixel is not within the acceptable limits the corresponding pixel location is marked in the difference image (step 131, 132). In both cases, a binary difference image of the array area is formed (step 133).

The edge template is formed by extracting low intensity regions from the color device template (step 120). Those regions are then expanded by performing dilation steps (step 121). The edge template is used as a reference to eliminate pixels in the difference image resulting from normal process variations and misalignment. A variable threshold value is obtained from and applied to the resulting difference image (step 124). A variable threshold value is selected for each image to eliminate minor differences due to normal process variations. Applying a variable threshold value to the difference image allows for devices that are different in color due to slight oxide/nitride film thickness variations to be more fairly compared to the device template.

The optimal variable threshold value is selected by analyzing a grey scale histogram of the difference image elements. Starting at the lowest intensity bin of the histogram, frequencies of adjacent bins are averaged and compared with a predetermined value. The bins where the average of adjacent frequencies exceeds the predetermined value provides the grey scale value to be used as the variable threshold value. The grey scale value of the lower of the two bins is used as the threshold value.

Using a variable threshold value insures the preservation of subtle defects in the array area. A constant predetermined threshold value may be used in place of the variable threshold value after comparison of the raw data to the device template is made, but a variable threshold value is more desirable for detecting subtle defects that are low in contrast.

The acceptable image parameters are then removed from the thresholded difference image (step 126). This step is similar to step 135 but in addition includes removal of all single pixel differences. The corrected binary difference image of the overall segment resulting from steps 118 through 126 is then combined with the binary difference image of the array area comparison (steps 128 through 133), forming a final difference image (step 136) having corrected image elements.

The corrected image elements and the solder pad data are then processed through a series of tests (step 137). In summary, these tests compare and analyze the image elements for defects and are further explained in reference to FIGS. 3 and 4. If the image elements and/or solder pad data pass the tests (meaning a defect is not vital to the performance of the chip, or there is not a defect) (step 138=yes), the device does not need any operator review (step 139). If it does not pass the test (the defect is suspect, or may be vital to the future performance of the chip after failing some the tests) (step 138=no), the unsatisfactory image elements are highlighted, alerting the operator that review is required (step 140).

Figure 3:
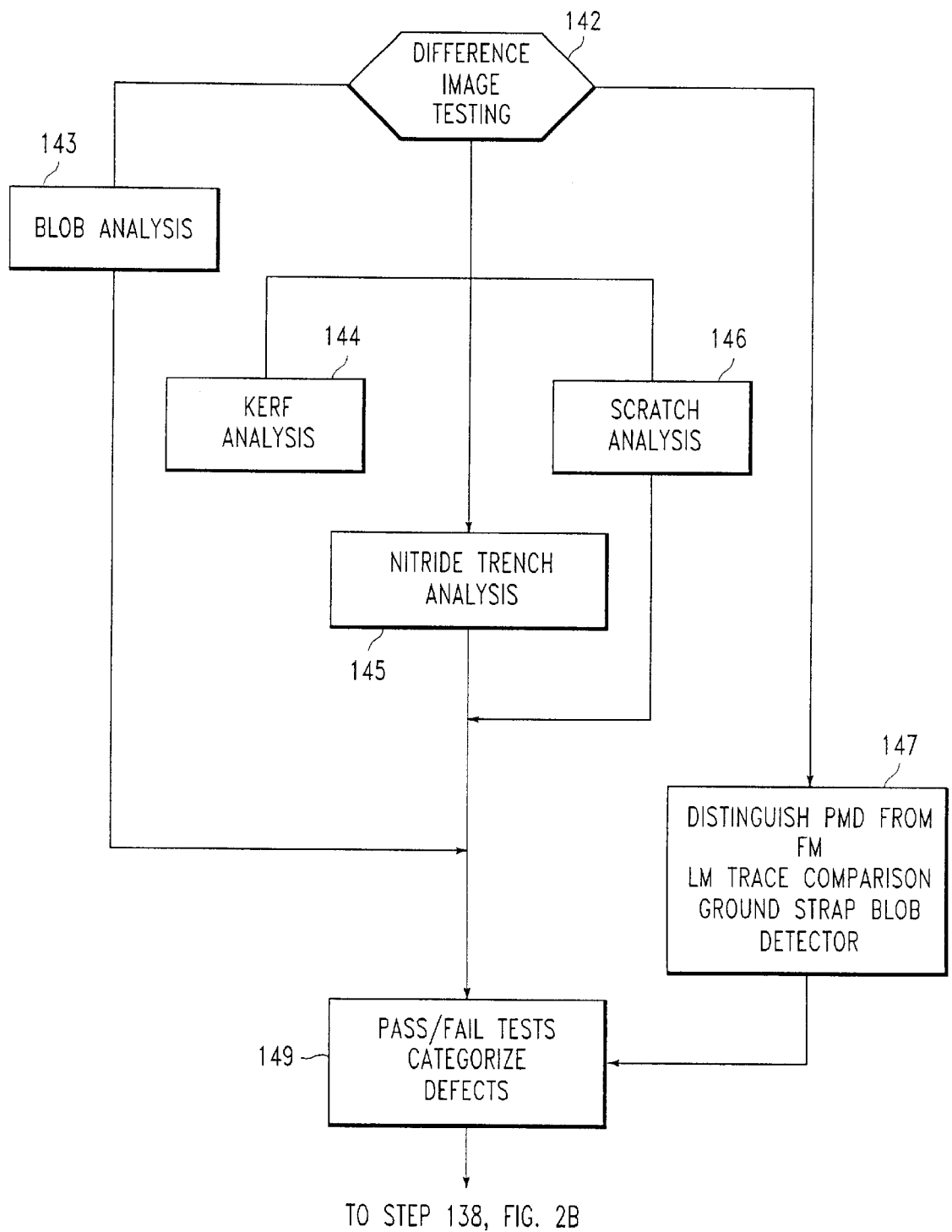
FIG. 3 is a flow diagram illustrating some of the tests of the imaging analogy of FIG. 2.

FIG. 3 shows a sampling of the tests used on the Difference Image to analyze the defects present (step 142). The tests include: BLOB Analysis (step 143), which is used to detect, to name a few, gross PMDs, gross miscuts, ECC, Misoriented Devices (M/O), large pieces of FM and large quantities of small particles, and large pieces of lifting kerf aluminum; Kerf Analysis (step 144), which is used to detect kerf width and lifting aluminum Nitride Trench Analysis (step 145), which is used to detect ECC and miscut defects; Scratch Test (step 146), which is used to detect moderate internal damage to the metal layers; and a series of tests: distinguishing PMD from Foreign Material (FM); LM Trace Comparison; and Ground Strap BLOB Detector (step 147). These tests generally provide acceptable criteria for image elements, compare the corrected image elements to the acceptable criteria as described below, and pass/fail the device accordingly (step 149). These tests may be performed simultaneously and thus are organized in branching tree arrangement within a library containing both image element parameters and image analysis procedures.

1. Blob Analysis

A BLOB is one or more black pixels within a difference image that are linked together through the rules of connectivity analysis (8-connectedness), which are well known in the art. For example each pixel in a BLOB has as one of its eight neighbors another pixel in the BLOB. The BLOB analyzer compares BLOBS in the difference image with parameters, such as shape, size, location, color, and quantity. The BLOB analyzer analyzes and categorizes the corrected image elements that do not correspond to the device template parameter values. BLOB analysis detects gross forms of external damage to the passivation layer/underlying metal structures. Thus, BLOB analysis is capable of detecting gross forms of ECC, M/O, PMD and Miscuts. BLOB Analysis also detects defects such as: delaminated aluminum and polyimide; gross forms of lifting kerf aluminum; residual resist on metal arrays; missing metal arrays, polyimides, and nitrides; gross forms of internal and external contaminants; damage-causing Foreign Materials (FM); gross forms of corroded metal arrays; and gross forms of internal damage under polyimide and over or under the etch of polyimide. An unacceptable amount of FM can be detected with this test.

2. Kerf Analysis

Kerf analysis insures that devices that are too large or too small due to miscuts are rejected. First, the distance from the outer edge of the nitride trench to the cut edge of the device (the image parameter values that make up the kerf region) is compared to a predetermined set of value(s). Two diagonal device corners with their corresponding edges are typically measured from the chip edge to the nitride trench to determine this distance for all four sides. Then, the rule that two edges of the dark region (the kerf) must be parallel and linear would be applied for the kerf to pass the width/length criteria. Also, regions of dark kerf material extending on for a length greater than the predetermined amount would be considered suspect for lifting kerf aluminum and would fail the test. This test detects lifting kerf metal that has not delaminated enough to cross over the nitride trench or lay over the active area of the chip, thus providing reliability testing for the device.

3. Nitride Trench Analysis

Figure 11A:
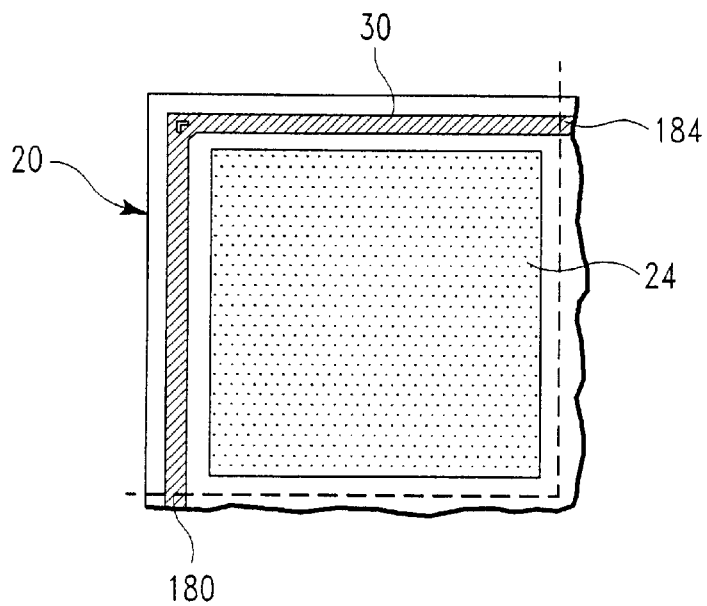
FIGS. 11A–11B and 12A–12B illustrate examples of accepted and rejected nitride trenches according to the analysis of the present invention.
Figure 12A:
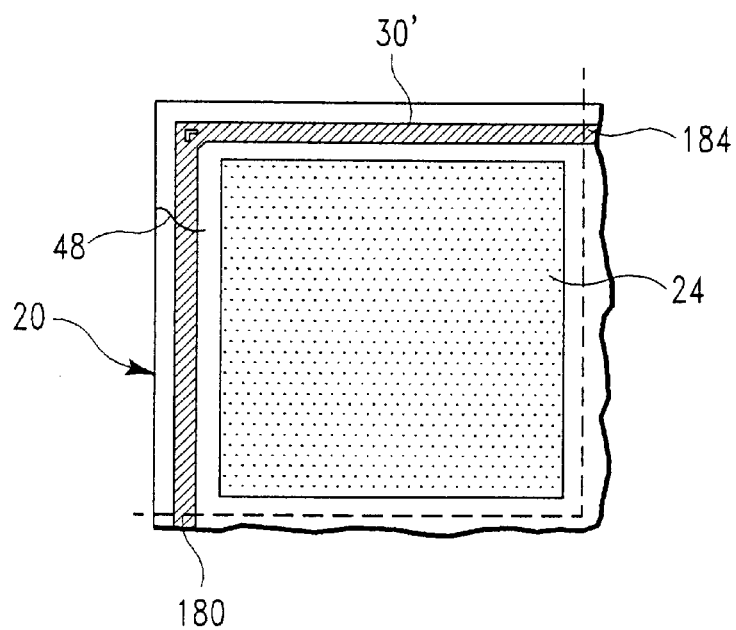

A section of semiconductor chip 20 containing normal nitride trench 30 is illustrated in FIG. 11A. Defective nitride trench 30' resulting from hairline edge crack 48 is shown in FIG. 12A. The nitride trench integrity analysis test begins with pixel 180 within trench 30 and links the acceptable pixels within trench 30 to form region 182 having an area almost identical with trench 30 if the trench is intact.

Figure 12B:
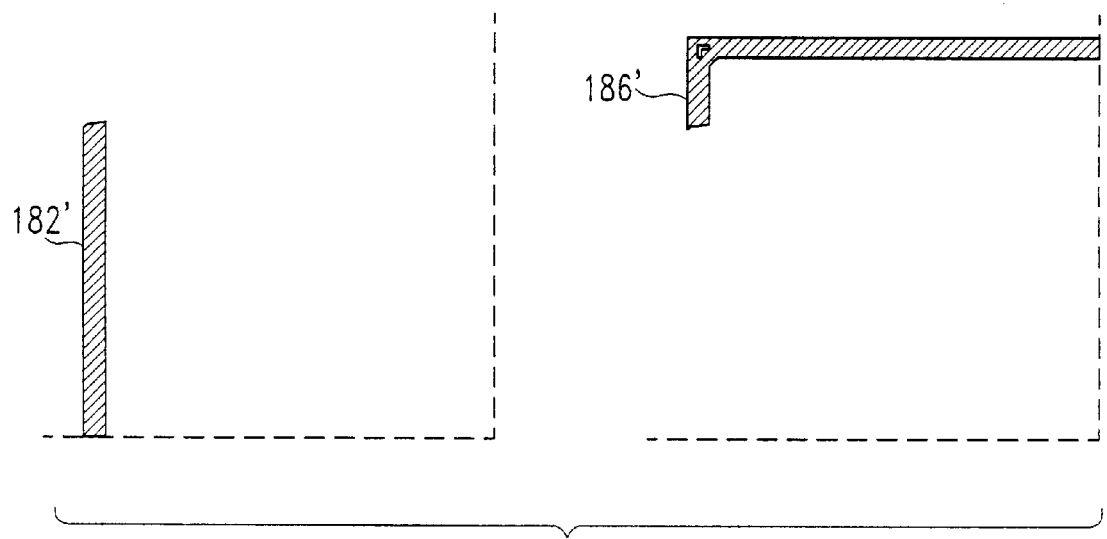

Each pixel in trench 30 is analyzed for its color value, and if the color is within an acceptable range of values, a corresponding pixel will be marked as acceptable within region 182 by a method such as setting the corresponding pixel in region 182 to black. Then the next neighboring pixel location will be analyzed, and again, if the color is within an acceptable range of color values, the corresponding pixel within region 182 will also be changed to black. Region 182 will have a continually growing black region, pixel by pixel, as long as the color of the nitride trench pixels remain within a set range of color values, allowing for graduated color variations from device to device (or even within one device). If there is an abrupt color change, however, region 182' growth stops as shown in FIG. 12B.

Figure 11B:
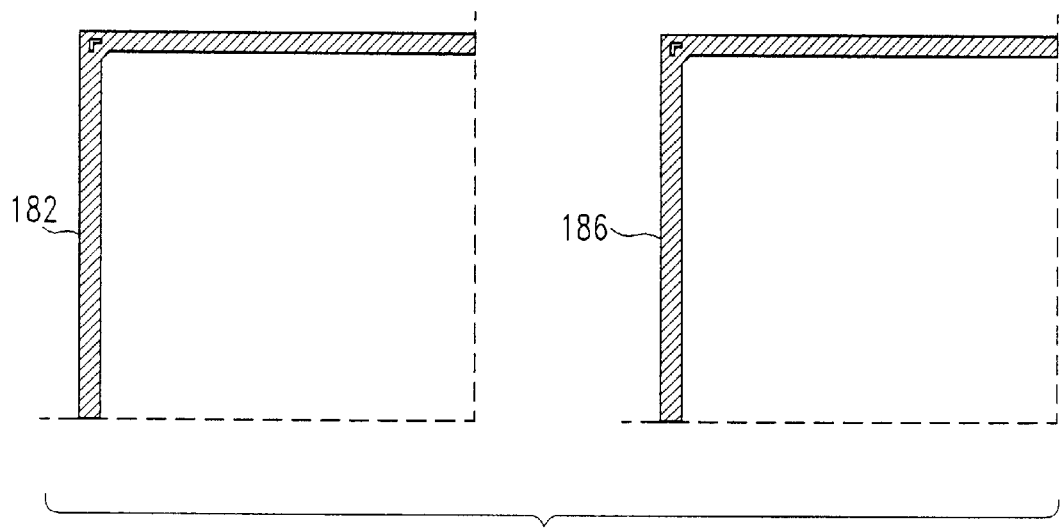

In the next step second starting pixel 184 is selected at a distance from first starting pixel 180. The color comparison and region building described hereinabove is repeated from this location and in a direction toward first starting pixel 180 to produce corresponding region 186. Two starting locations 180 and 184 are preferably specified within trench 30, where the trench intersects segment boundaries. The areas of regions 182 and 186 grown from each starting location are compared to one another. FIG. 11B illustrates regions of equal area 182 and 186 grown from two starting locations 180 and 184. Dissimilar areas 182' and 186' indicate a disruption in the continuity of trench 30' along crack 48 as shown in FIG. 12B. The nitride trench integrity analysis test is capable of detecting very fine forms of ECC and miscut defects in a trench which are not detectable by methods such as edge detection. In addition a minimum area check is performed to ensure that a symmetrical break in the trench at the midpoint is not accepted.

4. Scratch Test

The scratch test identifies thin scratches consisting of a series of small corrected image elements that may be only a pixel or two wide. These image elements are collectively analyzed to see if they make up a part of a line, or a scratch. Through the application of multiple passes of linear regression analysis, well known in the art, these small regions of data are preserved when benign image elements are removed, taking advantage of the fact that scratches are usually not perfectly vertical or horizontal, but are somewhat diagonal. Advantage may also be taken from the fact that scratches may also have an arc from operation of a spinning tool. Thus, minor comparison differences due to normal process variations, such as slightly thinner or wider lines, may be removed and will not be improperly classified as a scratch (these lines are identified and removed through the application of a Hough transform, well known in the art). In addition, the probability of the remaining small random image elements lining up to form a perfect line is very low. The Scratch Test is important since it detects CMP scratches due to a grinding/polishing step within wafer fabrication, handling damage scratches due to handling the metal prior to the passivation application, and cracks over M2 that are sometimes subtle in nature and not always continuous. A scratch need not be a continuous line. To distinguish discontinuous scratches from other BLOBS, a minimum length BLOB criterion is applied to BLOBS within an image to select those for inclusion in the regression analysis. To avoid false scratch characterizations there must also be a minimum number of BLOBS lined up to form the scratch, preferably at least four BLOBS.

5. Distinguishing PMD from FM

Distinguishing small FM from PMD over the metal area, such as a metal 1, metal 2 (M1/M2) array area is critical in successfully detecting PMD without having a high false positive rate. The majority of PMD defects over the M1/M2 array area have a characteristic hole in the center of the damage area. Thus, any BLOB in the difference image which contains a hole in its center is a PMD suspect. When this signature is present there is a high probability that it is due to an actual PMD and not FM. The more subtle forms of PMD are distinguished from FM since forms of PMD exhibit distinct color variations within the defect boundaries and forms of loose FM do not. This analysis is accomplished by examining the pixels within the original raw color image (as identified by the BLOB within the difference image) and comparing the color values of those pixels against a predetermined set of color values. If the pixels within the BLOB exceed the predetermined color values the defect is flagged as a PMD. In addition, the grey scale uniformity across a BLOB is used to distinguish FM from PMD.

6. LM Trace Reference Comparison

Because very small differences or corrected image elements in LM traces are not successfully identified by the BLOB Analyzer, it was necessary to develop a more sensitive testing technique to insure detection of fine cracks and damage. The fact that LM circuitry has a distinct color signature and high contrast edges allows extraction of LM's from the rest of the device (using color segmentation as described hereinabove). LM Trace Reference images are built from good device images for each segment. By comparing the LM Trace Reference to actual LM's on a device for a given segment, subtle differences in color and shape can be obtained. These differences are analyzed for shape, size, and location after the comparison output file is scrubbed of minute edge variations and thresholded. Parameters controlling the shape location and size of these differences determine if they are reported as areas requiring review. Hence, LM Trace Comparison Analysis finds defects such as missing metal, cracked LM, extra metal, bridged metal and corroded metal.

7. Ground Strap Blob Detector

The ground strap blob detector is used to detect defects within the ground strap which is a layer of metal that forms a line having two parallel edges and which resides around the perimeter of the device. The edges are first isolated by performing a thresholding step on the region which includes the ground strap and whose coordinates are specified in the segment profile. The thresholding step provides a binary image that contains a line for each of the two parallel edges.

The location of the edge lines is identified in the region through the application of a Hough transform. A mean grey scale value is obtained for the region between the two edge lines, and this mean grey scale value is used as a threshold value for a second thresholding step to obtain a binary image of the region between the two edge lines, thereby identifying pixels that could be defects. A second Hough transform is then applied to search for perpendicular line segments between the two edge lines. A perpendicular line segment that exceeds a specified length and width is flagged as a defect.

Solder Pad Analysis

Figure 4:
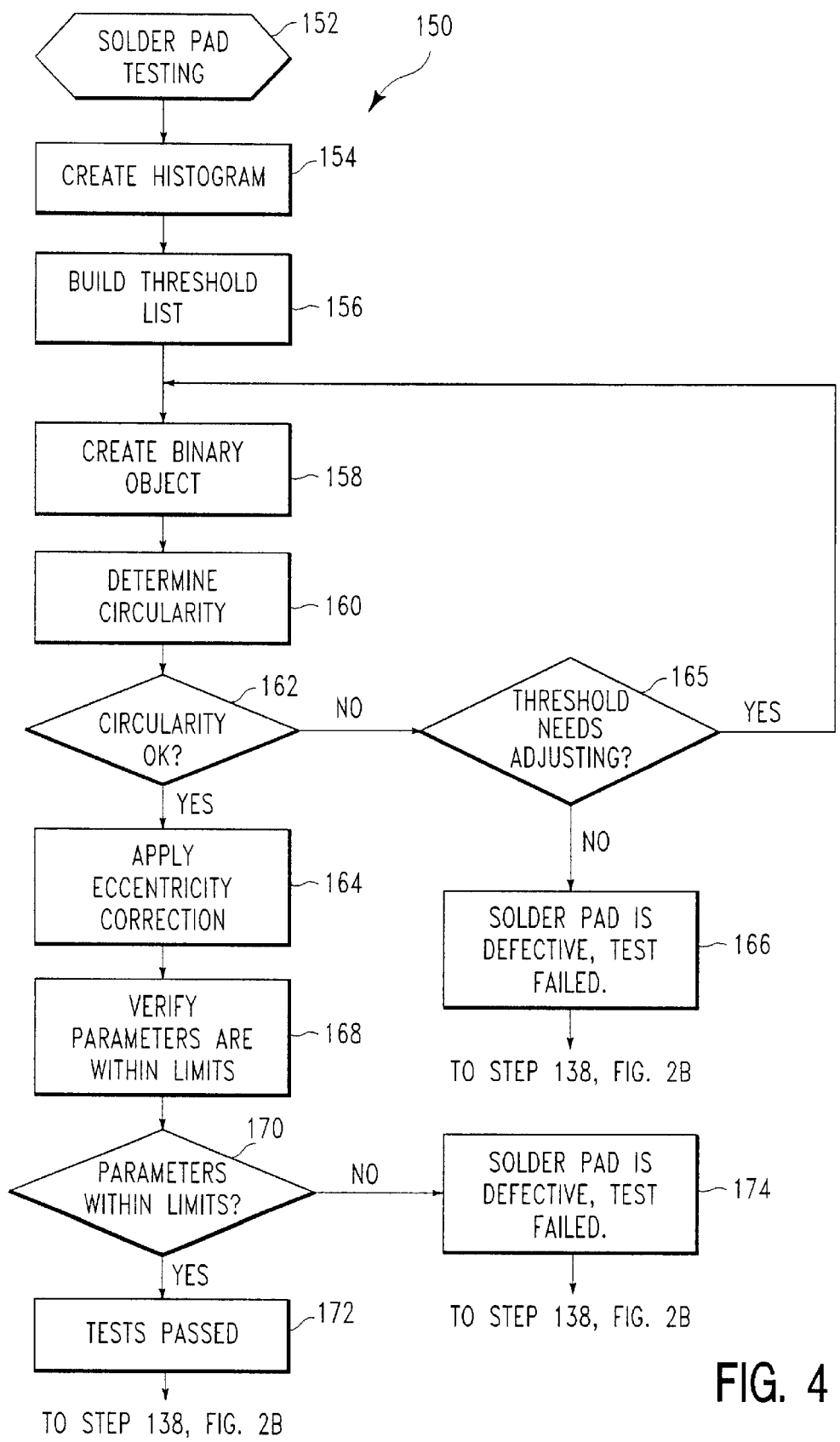
FIG. 4 is a flow diagram illustrating a test procedure of FIG. 2 for analyzing a device with solder pads.

FIG. 4 demonstrates the detecting of solder pad defects on a device 152. The resulting images and regions are then statistically analyzed for deviations from a list of requirements in a database that a good solder pad (such as a Controlled Collapse Chip Connection or "C4" pad) must meet. Consequently, a third dimension, (height) is not needed to achieve accurate results for detecting solder pad defects according to the present invention, since a slightly small diameter will equate to low volume solder pads.

Figure 5:
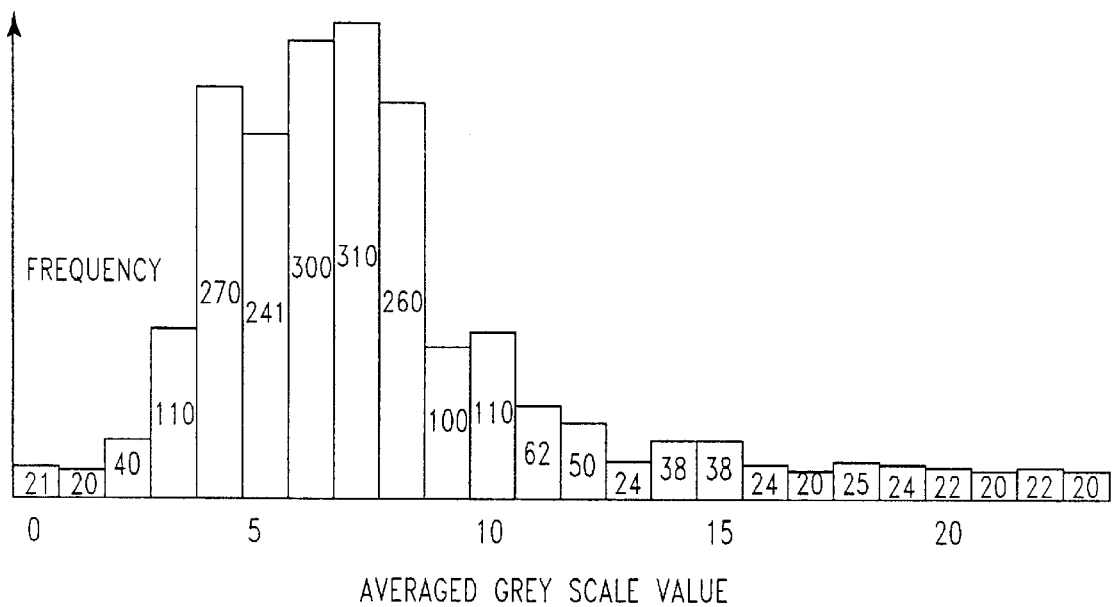
FIG. 5 illustrates a histogram of a solder pad region of FIG. 1 in which averaged grey scale value is plotted by frequency.

First, an averaged grey scale histogram is created from the solder pad data (step 154). Then, a threshold value list is built of the histogram (step 156), and a binary object is created (step 158). Image segmentation is accomplished by selection of an optimal threshold value which is applied to each solder pad image. The threshold value is obtained from the grey scale histogram (FIG. 5) by selecting the second maximum of the solder pad data after the first minimum of the solder pad data, (in the example of FIG. 5, the first minimum is at a grey scale of 5, and the second maximum after that minimum is at a grey scale of 10). Using the X/Y solder pad coordinate data within the segment profile, windows are defined around each solder pad location. The area within these windows then undergoes a two step erosion process to remove remaining trace lines and structures which are not part of the solder pad. Selection of the correct threshold value to be applied to each solder pad location is a critical step in the image segmentation process. The threshold value is selected through an adaptive technique where a resultant parameter (circularity)(step 160) is used to determine whether to repeat the thresholding step (step 162=no, step 165), or to accept the current output and continue to the next process (step 162=yes).

After passing the circularity check (step 160, step 162=yes), the other checks and analytical methods are performed (steps 164 and 168). The methods chosen for image solder pad analysis are circularity (step 160), eccentricity (step 164), and other tests (step 168) including: convexity, solder pad boundaries, relative and absolute surface areas, object center of mass, and relative and absolute radius, which verify that the parameters are within limits (step 170). If the parameters are within limits (step 170=yes) the pad is acceptable (step 172). Otherwise, the parameters are not within the desired limits (step 170=no), and the solder pad is defective (step 174).

Figure 6:
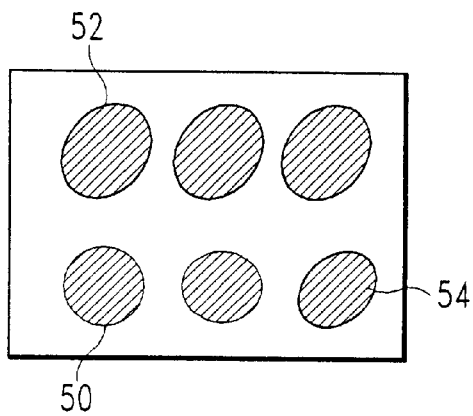
FIGS. 6, 7, 8, 9 and 10 illustrate examples of accepted and rejected solder pads according to the analysis of the present invention.

The circularity check is done to each solder pad in the segment. As shown in FIG. 6, in this example, a perfect solder pad 50 has a circularity value of 1.0. Due to the fact that some current solder evaporation processes deliver solder pads that may be elongated, but are still acceptable, an eccentricity correction factor may be applied. This correction compensates for elongated solder pads 52. It provides a more accurate representation of each solder pad's volume and is necessary for the successful detection of low volume pads 54 and the elimination of false positives.

Figure 10:
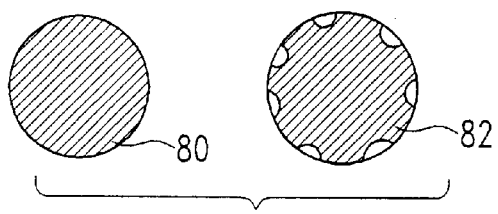

Referring to FIG. 10, a convexity check is done to each solder pad within the segment. This check is used to detect irregularities in the perimeter of a solder pad, which are characteristic of C4 FM defects. Included within the C4 FM defect category are: gross forms of solder pad corrosion 82, substrate fingers remaining on a solder pad post, Reduced Radius Removal (R3) processing, and miscellaneous types of FM which are on or touch a solder pad.

Figure 9:
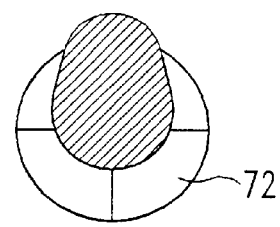

A boundary check is done to each solder pad in a segment to determine if any portion of the solder pad touches or extends beyond a predefined circular window 72, as shown in FIG. 9. The circular window 72 is positioned over the ideal solder pad center location. The size of the window is defined in the boundary check software and is used to detect solder pad Damage including Bridged solder pads, Grossly Misaligned solder pads, and Large Pieces of FM on solder pads.

Figure 7:
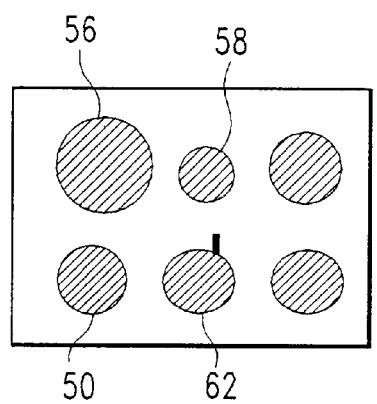
Figure 8:
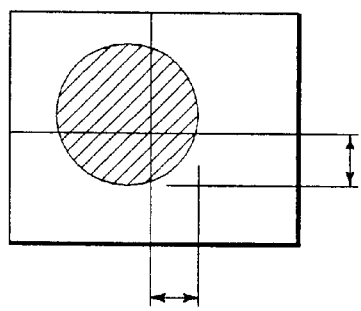

The object center of mass is determined for each solder pad in a segment. This calculated value is used to insure that a solder pad completely covers the nitride via, as shown in FIGS. 7 and 8. The via size is defined within the detection software and the via centers are defined in the segment profiles. The distance between a solder pad's center of mass and the nitride via center must not be greater than the minimum solder pad radius for the via to be properly covered. This check detects minor and grossly misaligned solder pads.

The absolute minimum and maximum surface area check is performed on each solder pad within a segment. If the area of any solder pad is not within these limits after the eccentricity correction factor has been applied, the solder pad fails the check. This check is capable of identifying some forms of low and high volume solder pad defects.

As seen in FIG. 7, the relative minimum and maximum surface area check is performed on all solder pads in a segment after excluding those pads which have unacceptable circularities from the average solder pad surface area calculation. The relative minimum and maximum surface area limits are defined within the detection software. Any solder pad which deviates from the segment average by more than the specified limits is highlighted for review. This check can detect gross and subtle forms of low and high volume solder pad defects. As aforementioned, the ability of the present invention to detect low volume solder pads through a combination of surface area comparison and eccentricity compensation, alleviates the need for third dimension testing to achieve accurate results.

Thus, the present invention discloses a method to test small, multi-layered devices having solder pads with a minimal amount of false positive results. In a series of experiments the false positive rate was 0.12% and with no defective solder pads going undetected. Furthermore, since the present invention utilizes a relatively low magnification for the semiconductor industry (i. e., approximately 50–100 times in magnification), defect detection is fast, but still accurate, due to the few segmented images that are captured and analyzed.

While the invention has been particularly shown and described with reference to a preferred embodiment thereof, it will be understood by those skilled in the art that the foregoing and other changes in form and details may be made therein without departing from the spirit and scope of the invention.

What is claimed is:

1. A method of analyzing visual inspection image data to find defects on a device under test, comprising the steps of:

a) providing a plurality of good devices;

b) imaging each of said good devices to provide a plurality of images of said good devices, said images of said good devices each comprising pixels;

c) comparing value of a first image parameter of each pixel of each good device to a first threshold value and converting said value to black or to white depending on whether said value is above or below said first threshold value;

d) deriving a device template image from said plurality of converted images of said good devices, said device template image comprising a device template image pixel corresponding to each good device pixel for said first image parameter;

e) providing the device under test;

f) imaging the device under test, to provide an image of the device under test comprising pixels corresponding to said pixels of said good devices;

g) subtracting said first image parameter of said device under test pixel by pixel from said template image to provide a difference image for said first image parameter;

h) comparing the value of each pixel of said difference image to a second threshold value;

i) converting the value of each pixel to black or white depending on whether the value of that pixel is above or below the second threshold value to generate a final corrected difference image; and j) identifying a defect on the device under test from said final corrected difference image.

2. The method of claim 1, wherein the device is a semiconductor integrated circuit chip.

3. The method of claim 1, wherein said first image parameter is one of color and grey scale.

4. The method of claim 1, further comprising the step of distinguishing passivation mechanical damage from foreign material by identifying a hole in the center of said corrected image elements.

5. The method of claim 1, further comprising the step of distinguishing passivation mechanical damage from foreign material by comparing one of color and grey scale uniformity within a suspected defect boundary for variation outside a specified range.

6. The method of claim 1, further comprising the step of distinguishing scratches from normal process variations by analyzing a series of said corrected image elements to determine if said corrected image elements are in a path of a straight line.

7. The method of claim 6, wherein in said step of distinguishing scratches, there are at least 4 said corrected image elements in said path.

8. The method of claim 1, further comprising the steps of:

providing a predetermined second threshold value for said difference image elements;

creating a histogram of said difference image elements; and selecting a variable threshold value at a point where the average of adjacent frequencies on said histogram exceed said predetermined second threshold value.

9. The method of claim 1, wherein said first image parameter includes at least one of size, shape, location, color, grey scale, contrast, and quantity.

10. The method of claim 1, wherein step c) further comprises the steps of:

c1) aligning each said device under test device under a microscope;

c2) providing an alignment template;

c3) comparing the alignment of said device with said alignment template in x, y and theta directions; and c4) realigning said device according to the comparisons of step (c3).

11. A method of analyzing visual inspection image data to find defects on a device under test, comprising the steps of comparing an image parameter value of a region of a device to a first color, pixel by pixel, until said image parameter value of said region deviate from a set range of color values to determine defects in said region.

12. A method of analyzing visual inspection image data to find defects in solder pads on a device, comprising the steps of:

a) providing a device having a first and a second solder pad;

b) imaging said first solder pad to provide a first solder pad image and imaging said second solder pad to provide a second solder pad image;

c) comparing said first solder pad image to said second solder pad image to detect a defect in one of said solder pads; and d) measuring said first solder pad image and comparing said measurement to a criterion comprising at least one of circularity, convexity, radius, surface area, center of mass, and eccentricity, wherein said criteria comprises a previously determined range of acceptable values.

13. The method of claim 12, wherein step b) further comprises the step of: analyzing a diameter of said first and said second solder pad image to determine a low volume solder pad.

14. The method of claim 12, wherein step b) further comprises the steps of:

b1) providing a range of acceptable circularity and a variable threshold value; and b2) thresholding said first and said second solder pad image with said variable threshold value if said first and said second solder pad image are within said range.

15. The method of claim 14, further comprising the steps of:

b3) averaging the surface areas of the first and the second thresholded solder pads image;

b4) providing a relative minimum and maximum surface area according to said average;

b5) comparing said first thresholded solder pad image with said minimum and maximum surface area; and b6) identifying a defect on said first solder pad image if said first solder pad image is not within said minimum and maximum surface area.

16. The method of claim 14, wherein step b1) further comprises the steps of creating an averaged grey scale histogram having a first minimum grey scale value and a second maximum grey scale value, said second maximum grey scale value having a larger value than said first minimum grey scale value; and selecting said second maximum grey scale value for said variable threshold value.

17. The method of claim 14, wherein in said providing step (a) providing a device having a plurality of solder pads, in said imaging step (b) imaging said plurality of pads, and in said comparing step (c) comparing said first solder pad image to an average of said plurality of solder pad images.

* * * * *